United States Patent [19]
Carion

[11] Patent Number: 5,437,622
[45] Date of Patent: Aug. 1, 1995

[54] TRANSPARENT ADHESIVE DRESSING WITH REINFORCED STARTER CUTS

[75] Inventor: Jean-Pierre Carion, Nieppe, France

[73] Assignee: Laboratoire Hydrex (SA), Montreuil, France

[21] Appl. No.: 51,484

[22] Filed: Apr. 22, 1993

[30] Foreign Application Priority Data

Apr. 29, 1992 [FR] France ................. 92 05250

[51] Int. Cl.⁶ .................. A61F 13/00; A61F 15/00
[52] U.S. Cl. ........................ 602/57; 602/41; 206/441; 128/853
[58] Field of Search .............. 602/41, 42, 57, 58, 602/59; 206/440, 441; 604/307, 304; 128/853, 854, 887, 888

[56] References Cited

U.S. PATENT DOCUMENTS

| | | | |
|---|---|---|---|
| 4,485,809 | 12/1984 | Dellas | 604/307 |
| 4,545,371 | 10/1985 | Grossmann et al. | 602/57 |
| 4,600,001 | 7/1986 | Gilman | 602/52 |
| 4,884,563 | 12/1989 | Sessions | 602/57 |
| 5,160,315 | 11/1992 | Heinecke et al. | 602/58 |

FOREIGN PATENT DOCUMENTS

| | | | |
|---|---|---|---|
| 1192825 | 9/1985 | Canada | 602/57 |
| 0066899 | 12/1982 | European Pat. Off. | |
| 0161865 | 11/1985 | European Pat. Off. | |
| 0189999 | 8/1986 | European Pat. Off. | |
| 0401949 | 12/1990 | European Pat. Off. | |

*Primary Examiner*—Paul Prebilic
*Attorney, Agent, or Firm*—Horst M. Kasper

[57] ABSTRACT

A transparent adhesive dressing of synthetic material having reinforced starter cuts is disclosed. The dressing contains three layers, namely, a sheet of flexible film made of polyurethane having an adhesive face, a protective sheet of backing covering the adhesive face, and a sheet of less flexible material made of polyethylene. A starter cut passes through at least two of the three layers. The starter cut is protected by a reinforcing strip disposed on the sheet of the less flexible film.

10 Claims, 1 Drawing Sheet

TRANSPARENT ADHESIVE DRESSING WITH REINFORCED STARTER CUTS

FIELD OF THE INVENTION

The present invention relates to a transparent adhesive dressing of synthetic material.

It relates more particularly to dressings commonly called "incision drapes" as used during surgical operations. Transparent adhesive dressings are also used for protecting the skin in the event of certain kinds of lesion, such as superficial burns or erythemas.

BACKGROUND OF THE INVENTION

During surgical operations in particular, an incision drape is applied to adhere to the site of the operation, i.e. the region of the skin of the patient in which an incision is to be made. The incision is made simultaneously through the incision drape and through the skin. The incision drape is removed after the operation.

The use of incision drapes has the advantage of increasing the accuracy of incision, of facilitating the handling of the skin around the incision, and of reducing the risk of infection.

Incision drapes are commonly constituted by a piece of flexible film, e.g. of polyurethane, which is cut from a roll. The adhesive face of the incision drape is protected by a backing, usually a sheet of paper which is removed at the moment of use. The two side edges of the incision drape include strips for grasping, e.g. strips of paper or of plastic that facilitate handling during installation on the site of the operation. The strips for grasping are generally secured to the piece of flexible film that constitutes the incision drape via respective lateral margins of said piece of flexible film to which they adhere. They may also be used for removal purposes after the incision drape has been used.

Given the extreme fineness and flexibility of a piece of polyurethane or other flexible film, known incision drapes suffer from the following drawback: when the backing or protection sheet is removed from the incision drape prior to its application on the site of the operation, the flexible film tends to twist and to crumple, with its adhesive face sticking to itself, thereby creating stuck-together creases which make the dressing unsuitable for use. Known products are not easy to handle and the amount of waste due to the adhesive face sticking to itself prior to application on site is large.

To mitigate the above-described drawback, proposals have been made, for example, to provide a dressing in which the entire periphery of the non-adhesive face is provided with a protective strip, e.g. of paper, thereby constituting a frame for laying purposes. The frame is intended to impart a certain amount of stiffness to the dressing prior to its application on site. The dressing is used as follows: the piece of transparent flexible film together with its laying frame disposed on its non-adhesive face are removed from the protective sheet; the dressing held by its frame is applied to the site; and the laying frame is removed.

That proposal constitutes an improvement over known dressings, at least when the dressings are small in size, since the polyurethane window or other flexible film held by the laying frame is very small and the tendency of the polyurethane film to twist and stick to itself is small. That technique is not suitable for incision drapes of larger dimensions, e.g. 15 cm×28 cm, since the area of the polyurethane film is too large to avoid the risks of its sticking.

To facilitate installing incision drapes and to increase safety in use, it would be desirable to impart greater stiffness not only to the periphery of the incision drape, but also to its entire area, even though said area is very fine and flexible in nature.

OBJECT AND SUMMARY OF THE INVENTION

Consequently, an object of the present invention is to provide a transparent adhesive dressing of synthetic material, in particular an incision drape, of the type described above and which can be handled much more reliably so as to avoid large quantities of waste, and so as to increase safety and rapidity of use while keeping costs as low as possible.

To achieve these objects, the present invention provides a transparent dressing of synthetic material:

which is constituted, prior to application, by three layers, namely a sheet of flexible film, in particular of polyurethane, having an adhesive face, a protective sheet or backing covering said adhesive face, and a sheet of less flexible material, in particular polyethylene, disposed on the non-adhesive face of the flexible film;

in which each of its lateral edges includes a strip for grasping assembled to the sheet of flexible film to which it adheres;

in which its useful area extending between the lateral strips for grasping is delimited, at least on one lateral side of the dressing, by a starter cut passing through at least two of the three layers; and in which at least one of the lateral starter cuts is protected by a reinforcing strip disposed on the sheet of less flexile film, in particular the sheet made of polyethylene.

The dressing of the invention has the advantage of having sufficient stiffness prior to application on site to enable it to be handled easily. Any risk of the polyurethane portion twisting, crumpling, and sticking to itself is thus avoided.

Given that the continuous polyurethane strips from which dressings or incision drapes are cut in order to prepare products ready for use are themselves manufactured using a polyethylene protective sheet which adheres to the non-adhesive face of the dressing by a static phenomenon, the preparation of single-use sterile dressings or incision drapes ready for use requires no additional preparatory step and gives rise to no increase in cost.

According to the invention, the sheet of flexile film is advantageously made of polyurethane, while the lesser flexible sheet is made of polyethylene. Polyurethane is a microporous material which is permeable to water vapor and to oxygen but which prevents any bacteria penetrating from the outside. Any other equivalent material can be used in the context of the present invention.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The invention is described in purely indicative manner with reference to the accompanying drawing given by way of non-limiting example.

MORE DETAILED DESCRIPTION

Figure 1:
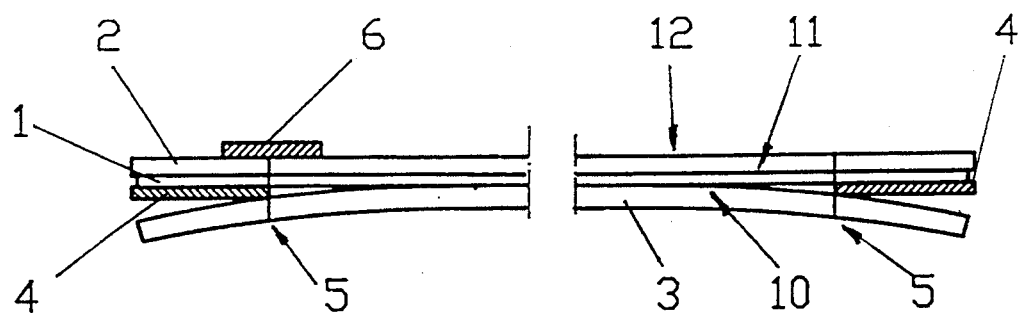
FIG. 1 is a section through a first embodiment of an adhesive dressing of the invention, and including two lateral starter cuts.

A nomenclature of the various references used in the course of the description can be found at the end thereof.

A dressing, for example, an incision drape, is constituted by three layers:

a sheet of flexible film 1 of synthetic material and possessing an adhesive face 10 and a non-adhesive face;

a protective sheet or backing 3 for the adhesive face 10; and a sheet of less flexible film material 2 disposed on the non-adhesive face of the flexible sheet 1.

In the context of the present invention, it is particularly advantageous to provide for the sheet of flexible film 1 to be made of polyurethane and for the sheet of less flexible film 2 to be of polyethylene.

Since polyurethane is a microporous material, it has the advantageous of allowing water to evaporate and of avoiding any maceration between the incision drape and the skin, while preventing bacteria penetrating from the outside, thereby reducing the risk of infection.

In addition, since the presence of the polyethylene film is necessary during manufacture of the continuous rolled-up strips of polyurethane from which the sterile dressings are cut off and prepared ready for use, the type of manufacture in accordance with the invention does not imply any increase in cost.

However, in the context of the present invention, it is also possible for the sheet of flexible film to be made of some other material that satisfies the same criterion as polyurethane. The same is true of the sheet of less flexible material which is intended solely to impart a degree of stiffness to the dressing prior to and during application on site.

In a preferred embodiment of the invention, as shown in FIG. 1, each of the lateral edges of the dressing includes a strip 4 for grasping, e.g. a strip of colored synthetic material, which strip is disposed between the polyurethane sheet 1 and the protective sheet or backing 3. The strip for grasping 4 is assembled to the polyurethane film 1 to which it adheres. The useful area 12 of the dressing is delimited on opposite sides by respective starter cuts 5 that pass through all three layers 1, 2, and 3 of the dressing. A reinforcing strip 6 is advantageously disposed over one of the starter cuts 5 to facilitate assembly with the polyethylene film 2.

The dressing of the present invention is very easy and safe to apply. The presence of the polyethylene sheet 2 imparts to the dressing proper, i.e. to the polyurethane sheet 1, the stiffness required to prevent it twisting and sticking to itself.

The dressing corresponding to the embodiment shown in FIG. 1 is applied as follows: firstly the protective sheet or backing 3 is removed from the adhesive face 10 of the polyurethane sheet 1 which, at this stage, remains assembled with the polyurethane sheet 2 by a static phenomenon; the dressing is applied to the site of the operation; the strip for grasping 4 is removed by tearing along the starter cuts 5 that are not protected by a reinforcing strip 6; and then the second strip for grasping 4 is removed together with the polyethylene sheet 2 which is separated very easily from the polyurethane sheet 1.

The width of reinforcing strip 6 is smaller then the distance between the set of starter cuts 5 and a respective neighboring edge of the sheet 1.

Figure 2:
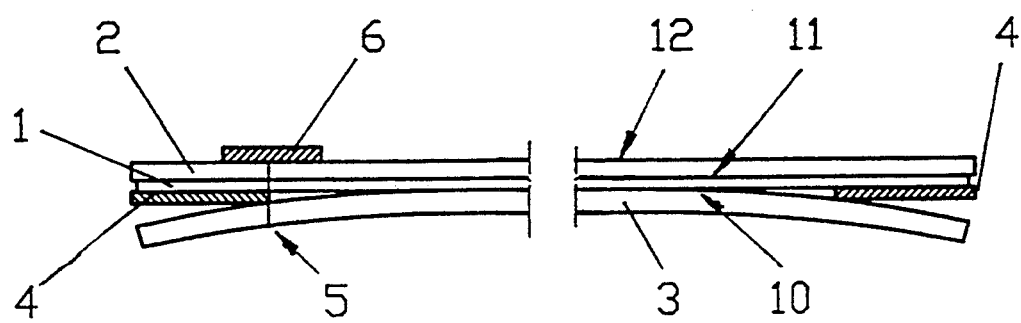
FIG. 2 is a section through a second embodiment of an adhesive dressing of the invention, including one lateral starter cut.

In another embodiment of the invention as shown in FIG. 2, it is similarly possible to provide a single lateral starter cut 5 passing through all three layers 1, 2, and 3, but only along one of the lateral sides of the dressing. The starter cut then includes a reinforcing strip 6.

A dressing including only one lateral starter cut 5 is applied as follows: as before, the protective sheet or backing 3 is initially removed from the adhesive face 10 of the polyurethane sheet 1 whose non-adhesive face 11 is protected by a sheet of polyethylene 2 that adheres thereto by a static phenomenon; the dressing is applied to the site of the operation; and then the strip for grasping 4 is removed together with the polyethylene sheet 2 by tearing along the single starter cut 5 which is protected by a reinforcing strip. The strip for grasping 4 disposed along the lateral side that does not include a starter cut remains attached to the polyurethane sheet 1 while it is applied to the site of the operation. The strip for grasping that remains in place facilitates removal of the dressing from the site of the operation after it has been completed. This embodiment is particularly suitable for dressings that are large in size.

Figure 3:
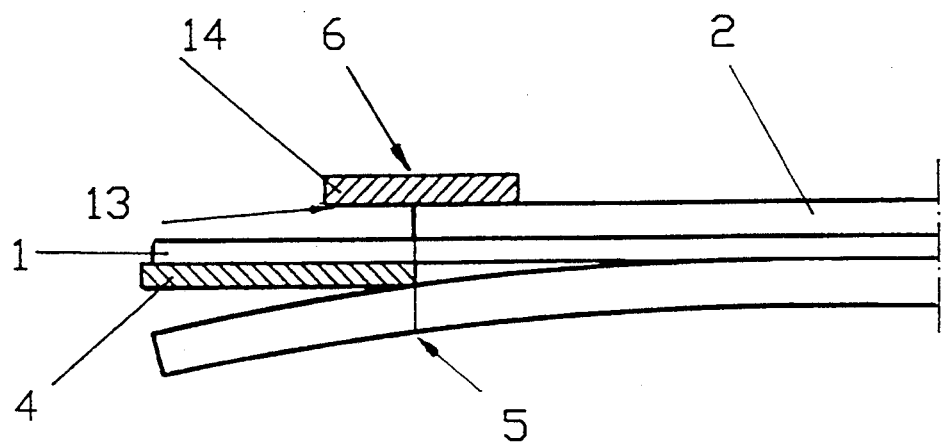
FIG. 3 is a fragmentary section through a third embodiment of an adhesive dressing of the invention, including a projecting reinforcing strip.

FIG. 3 shows a particularly advantageous embodiment of an adhesive dressing of the invention. The dressing is made up as described above, but on one lateral side the polyethylene sheet 2 extends only as far as the starter cut 5 so that the reinforcing strip 6 projects over said sheet of flexible film 1. The bottom surface 13 of the projecting portion 14 of the reinforcing strip 6 is then not adhesive.

The dressing shown in FIG. 3 is applied as follows: as before, the protective sheet or backing 3 is initially removed from the adhesive face of the polyurethane sheet 1 whose non-adhesive face is protected by a sheet of polyethylene 2 that serves as a stiffener and that is assembled to the sheet 1 by a static phenomenon; thereafter the dressing is applied to the site of the operation; and then the protective polyethylene film 2 is removed by raising the projecting reinforcing strip 6, advantageously while using the other hand to hold the strip for gasping 4 disposed on the same lateral side as the reinforcing strip 6, so that the strip 6 also serves as a removal strip. The strips for grasping can be left in place during the operation. They facilitate removal of the dressing from the site of the operation after it has been completed.

| NOMENCLATURE |
|---|
| 1 Sheet of flexible film, e.g. polyurethane. |
| 2 Sheet of less flexible material, e.g. polyethylene. |
| 3 Protective sheet. |
| 4 Strip for grasping |
| 5 Lateral starter cut. |
| 6 Reinforcing strip. |
| 10 Adhesive face of the sheet of flexible film 1. |

NOMENCLATURE (continued)

11 Non-adhesive face of the sheet of flexible film 1.
12 Useful are of the dressing.
13 Bottom face of the projecting portion 1 of the strip 6.
14 Projecting portion of the reinforcing strip 6.

I claim:

1. A transparent adhesive dressing of synthetic material comprising
    a first layer formed as a sheet of flexible film having an adhesive face and having a non-adhesive face;
    a second layer forming a protective sheet backing covering said adhesive face;
    a third layer formed as a sheet made of a less flexible material disposed on the non-adhesive face of the sheet of flexible film;
    a first strip for grasping disposed at a first lateral edge of the sheet of flexible film, wherein the first strip for grasping adheres to the sheet of flexible film;
    a second strip for grasping disposed at a second lateral edge of the sheet of flexible film, wherein the second strip for grasping adheres to the sheet of flexible film;
    wherein a useful area of the transparent adhesive dressing is extending between the first strip for grasping and the second strip for grasping;
    starter cuts passing through at least two of the three layers and disposed along the first lateral edge of the sheet of flexible film;
    a reinforcing strip disposed on the sheet of less flexible film for protecting said starter cuts.

2. The transparent adhesive dressing of synthetic material according to claim 1, wherein a first side of the sheet of less flexible material extends no further than the starter cuts such that the reinforcing strip projects over said sheet of flexible film, wherein a bottom face of a projecting portion of the reinforcing strip is not adhesive.

3. The transparent adhesive dressing of synthetic material according to claim 1, wherein the sheet of flexible film of the first layer is made of polyurethane.

4. The transparent adhesive dressing of synthetic material according to claim 1, wherein the less flexible material forming the third layer is made of polyethylene.

5. A transparent adhesive dressing of synthetic material comprising
    a sheet of flexible film having an adhesive face and having a non-adhesive face;
    a protective sheet disposed adjacent to the sheet of flexible film and forming a backing covering said adhesive face;
    a sheet made of a material, which is less flexible than a material employed for the sheet of flexible film and disposed on the non-adhesive face of the flexible film and wherein the sheet of flexible film, the protective sheet and the sheet made of a material, which is less flexible than the material employed for the sheet of flexible film, form a three layer structure;
    a first strip for grasping attached to a first lateral edge of the three layer structure and adhering to the sheet of flexible film;
    a second strip for grasping attached to a second lateral edge of the three layer structure and adhering to the sheet of flexible film wherein a useful area of the three layer structure extends between the first strip for grasping and the second strip for grasping;
    a first set of starter cuts passing through at least two layers of the three layer structure, and wherein the first set of starter cuts delimits grasping at least on one of the first lateral side and of the second lateral side of the three layer structure forming the dressing; and
    a reinforcing strip disposed on the sheet of less flexible film for protecting the area of the first set of starter cuts passing through at least two layers of the three layer structure.

6. The transparent adhesive dressing of synthetic material according to claim 5, wherein a first lateral side of the sheet of less flexible material extends no further than the first set of starter cuts such that the reinforcing strip projects over said sheet of less flexible material, a bottom face of the projecting portion of the reinforcing strip not being adhesive.

7. The transparent adhesive dressing of synthetic material according to claim 5,
    wherein the sheet of flexible film is made of polyurethane;
    wherein the sheet made of a material, which is less flexible than the material employed for the sheet of flexible film, is polyethylene.

8. The transparent adhesive dressing of synthetic material according to claim 5, wherein the protective sheet extends over the area of the first strip and of the second strip without adhering to the first strip and without adhering to the second strip.

9. The transparent adhesive dressing of synthetic material according to claim 5, wherein the sheet of flexible film, the protective sheet, the sheet made of a material, which is less flexible than the material employed for the sheet of flexible film, and a respective one of the first strip for grasping and of the second strip for grasping extend laterally to substantially the same respective lateral edge.

10. The transparent adhesive dressing of synthetic material according to claim 5, wherein the width of the reinforcing strip is smaller than the distance between the set of starter cuts and a respective neighboring edge of the flexible film.

* * * * *